United States Patent [19]

Marszal et al.

[11] Patent Number: 6,033,868
[45] Date of Patent: Mar. 7, 2000

[54] IN VITRO BIOSYNTHESIS OF PROTEINS IN NATIVE CONFORMATION

[75] Inventors: Ewa Marszal, Logan; William H. Scouten, Providence, both of Utah

[73] Assignee: Utah State University, Logan, Utah

[21] Appl. No.: 08/739,937

[22] Filed: Oct. 30, 1996

Related U.S. Application Data

[63] Continuation-in-part of application No. 08/339,465, Nov. 14, 1994, abandoned.

[51] Int. Cl.⁷ .............................. C12P 21/06; C12N 9/00; C12M 1/36
[52] U.S. Cl. ...................... 435/69.1; 435/183; 435/289.1
[58] Field of Search ................................ 435/69.1, 289.1, 435/183

[56] References Cited

U.S. PATENT DOCUMENTS

| | | | |
|---|---|---|---|
| 4,362,669 | 12/1982 | Verlander et al. | 422/131 |
| 4,748,124 | 5/1988 | Vogler | 435/240.241 |

FOREIGN PATENT DOCUMENTS

94/06928  3/1994  WIPO .

OTHER PUBLICATIONS

Scouten, W.H. et al. "Immobilized cell free protein synthesis system" Journal of Molecular Recognition (Oct. 1993), vol. 6, No. 1, p. 4.

Komar, A.A. et al. "Cotranslational heme binding to nascent globin chains" FEBS Letters (Jul. 1993), vol. 326, No. 1,2,3, pp. 261–263.

Denisov, I.G. "Thermal stability of proteins in intermolecular complexes" Biophysical Chemistry (Aug. 1992), vol. 44, pp. 71–75.

Kigawa, T. et al. "A continuous cell–free protein synthesis system for coupled transcription–translation" Journal of Biochemistry (1991), vol. 110, pp. 166–168.

Spirin, A.S. et al. "A continuous cell–free translation system capable of producing polypeptides in high yield" Science (Nov. 1988), vol. 242, pp. 1162–1164.

*Primary Examiner*—Robert A. Wax
*Attorney, Agent, or Firm*—Thompson E. Fehr

[57] ABSTRACT

A method for the in vitro biosynthesis of proteins in native conformation which improves the technique which is well known in the art by immobilizing on the surface of an affinity matrix at discrete locations a ligand for which the protein being synthesized has an affinity and adding to the reaction mixture said affinity matrix having said immobilized ligand so that each molecule that is in the process of folding into a functional protein molecule may bind an immobilized ligand and be kept separated from other protein molecules as the folding proceeds. The technique works with either a batch method or a continuous method.

2 Claims, No Drawings

IN VITRO BIOSYNTHESIS OF PROTEINS IN NATIVE CONFORMATION

CROSS-REFERENCE TO RELATED APPLICATION

This is a continuation-in-part of U.S. application Ser. No. 08/339,465, filed on Nov. 14, 1994, now abandoned.

BACKGROUND OF THE INVENTION

1. Field of the Invention

This invention relates to an improved method for the biosynthesis of proteins.

2. Description of the Related Art

There are several methods for synthesizing proteins.

One method is in vivo synthesis. In vivo synthesis has been the primary method for synthesizing proteins because it has produced higher yields than has in vitro synthesis. But a main disadvantage of in vivo synthesis of recombinant proteins is that the proteins produced by in vivo synthesis are often improperly folded.

As suggested in the preceding paragraph, a second major category of synthesizing proteins is in vitro biosynthesis. As used herein, in vitro biosynthesis means cell-free protein synthesis using either mRNA (translation system) or its complementary DNA (coupled transcription/translation system) as the template for protein synthesis, which is added to a cell extract containing the other biological components, e.g., ribosomes, t-RNAs, aminoacyl-tRNA synthetases, nucleotides, amino acids, etc., needed for protein synthesis.

Classical cell-free protein synthesis in a batch mode is, however, inefficient, i.e., it produces a low yield of the desired proteins. And continuous-flow cell-free synthesis has two significant disadvantages. Although continuous-flow cell-free synthesis as proposed by Spirin (Spirin, A. S. et al. (1988), *Science* 242, 1162–1164) initially produces a good yield, the desired rate of protein production does not continue for a sufficiently long time to be commercially useful, possibly due to the elution of important components, such as proteins and tRNAs, from the reactor through a semipermeable membrane (Endo, Y. et al. (1992), *J. Biotech.* 25, 221–230). Also, other researchers have determined that the activity of synthesized enzymes produced by this method decreases with the time of the synthesis reaction due to defects in protein folding. Misfolding is thought also, at least in part, to cause clogging of the semipermeable membrane in a continuous system. (Kudlicki, Wieslaw; Kramer, Gisela; and Hardesty, Boyd, "Cell Free System for Protein Synthesis and Use of Chaperone Proteins Therein," International Application Number PCT/US94/03860, International Publication Number WO 94/24303, International Publication Date Oct. 27, 1994 and Nishimura, Norihiro; Kitaoka, Yoshittisa; and Niwano, Mitsuru (1995) "Enhancement of Protein Synthesis in Continuous-Flow, Cell-Free System by Improvement of Membrane Permeation," *Journal of Fermentation and Bioengineering*, volume 80, number 4, pp. 403–405)

Furthermore, the yield of the protein synthesized by a third distinct technique for synthesizing proteins, i.e., a chemical method, such as the one used by Merrifield and described in Merrifield, B. (1986) *Science* 232, 341–347, unfortunately decreases with the length of the synthesized protein. This is due to the fact that errors are introduced because the coupling of each amino acid to the partially completed polypeptide chain is not one hundred percent efficient. The population of proteins with such errors, i.e., amino acid deletions, increases with each amino acid addition. For this reason it is not commercially feasible to make large quantities of long polypeptide chains with this method.

To produce a high yield of desired proteins, it would, therefore, be advantageous to have a continuous-flow cell-free technique which produces properly folded proteins.

In a cell, protein folding is assisted by at least two groups of proteins, viz., (1) enzymes (such as protein disulphide isomerase and peptidyl prolyl cis-trans isomerase) which catalyze isomerization of specific peptide bonds and (2) molecular chaperones (e.g., proteins of the hsp70). hsp90, and chaperonin (GroEL/hsp60) families) which prevent inappropriate protein-protein interactions that would, if not prevented, lead to incorrectly folded and, thus, inactive, proteins. However, these naturally existing systems which assist protein folding often fail upon a synthesis of large quantities of recombinant protein, both in cells and in cell-free systems. This, consequently, leads to the production of large quantities of inactive protein.

The present inventors are, furthermore, aware that an affinity matrix has been utilized to isolate a protein during renaturing as part of a rather complicated process. In that process proteins were synthesized in cells. Then the cells were broken. The synthesized eukaryotic proteins were then in an agglomeration. Therefore, such proteins had to be denatured. The affinity tag and the affinity matrix were employed in the subsequent renaturing—for cases when renaturing could, in fact be achieved—to isolate the protein and sometimes achieve proper folding.

SUMMARY OF THE INVENTION

The inventors' general technique is to maintain proteins that are synthesizing apart from one another so that they can fold properly. A solid matrix is a preferred way to achieve this status. The present invention, therefore, preferably, overcomes such improper folding by using a solid matrix which has an affinity for the proteins that are synthesized.

Protein molecules will then bind to the matrix either during biosynthesis or immediately after biosynthesis, as soon as their binding site has been formed. The concentration of the newly synthesized protein molecules in the solution will thereby be considerably decreased. And this binding of newly synthesized proteins (or proteins undergoing synthesis) prevents agglomeration of the molecules that are transiently in a partially unfolded state.

Consequently, as discussed above, each protein molecule that is synthesized will be kept away from other synthesized protein molecules; and this will aid their proper folding.

An affinity ligand present on the surface of the solid matrix not only enables binding of the protein to the solid matrix, but also may serve as a template to guide the folding of the synthesized protein. It should be understood that, in this context, a template is a molecule, or set of molecules, around which a protein can fold to assume that shape which is necessary for protein activity.

And unlike the utilization of an affinity tag and an affinity matrix in the prior art, the present preferred embodiment has fewer steps: the in vitro biosynthesis is followed immediately by elution. Moreover, the present method avoids agglomeration of the proteins.

DESCRIPTION OF THE PREFERRED EMBODIMENT

The present method is applied under conditions that are well known in the art of biosynthesizing proteins, such as those for temperature, pH, buffers, concentration, and the like. Similarly, other than those ligands associated with the introduced solid matrix, the components, utilized may be any of those which are commonly used in the art for the biosynthesis of proteins. Any of the protocols known in the art for protein biosynthesis can be followed (e.g., Zubay, G. (1973) *Annu. Rev. Genet.* 7, 267–287; Roberts, B. E. and Paterson, B. M. (1973) *Proc. Natl. Acad. Sci. USA* 70, 2330–2334; Marcus, A. et al. (1974) *Methods in Enzymology* XXX, 749–754 Academic Press, New York; Pelham, H. R. B. and Jackson, R. J. (1976) *J. Biochem.* 67, 247–256; Gasior, E. et al. (1979) *J. Biol. Chem.* 254, 3965; Erickson, A. H. and Blobel, G. (1983) *Methods in Enzymology* 96, 38–50, Academic Press, New York; Morch, M. D. et al. (1986) *Methods in Enzymology* 118, 154–164, Academic Press, New York; Kudlicki et al. (1992) *Anal. Biochem.* 206, 389–393) or commercial systems can be utilized (e.g., those from Promega, from Ambion, or from Amersham).

The present method can either start with DNA as a source of genetic information and subsequently synthesize the proteins by coupled transcription/translation wherein mRNA is created as an intermediate product or, alternatively, start with mRNA as a source of genetic information and synthesize the proteins through translation alone.

The requisite reactions occur in a container designated the in vitro biosynthesizing reactor.

Any of the components which are well known in the art to be adequate for biosynthesizing proteins are placed into this in vitro biosynthesizing reactor, as also is the desired solid matrix, which has immobilized on its surface at numerous discrete locations a ligand selected from the group consisting of substrate analogues, transition state analogues, other inhibitors, antibodies, and prosthetic groups, where for the present method prosthetic group means a nonpeptide molecule, bound to a protein, that is essential for the protein function. The solid matrix (which can, for example, be either a gel or hollow fibers) provides a support for the ligands immobilized to it and distributed at discrete locations on the solid matrix. A satisfactory gel can be any of those which are commonly used in affinity chromatography, but POROS (PerSeptive Biosystems) is preferred because it has a system of very large pores that enable the synthesizing proteins and the newly synthesized proteins to have direct contact with the ligand.

The choice of a specific ligand depends upon which specific protein one desires to synthesize since the ligand must be one for which that specific protein has an affinity. For example, methotrexate can serve as a ligand for dihydrofolate reductase; dehydroluciferin, for firefly luciferase; flavin mononucleotide (FMP), for bacterial luciferase or other FMP binding proteins; heme, for globin and other heme binding proteins; and pyridoxal phosphate, for pyridoxal phosphate binding proteins, e.g., tyrosine aminotransferase. As a guide to the choice of a preferred, books from the area of affinity chromatography can be consulted, e.g., Scouten, W. H. (1981) *Affinity Chromatography: Bioselective Adsorption on Inert Matrixes,* Wiley & Sons, New York, and Turkova, Jaroslava (1993) "Bioaffinity Chromatography," *Journal of Chromatography Library,* volume 55, Elsevier, Amsterdam.

In the absence of the ligand, protein molecules in the synthesis mixture exist in many conformations. Some conformations that are partially unfolded cause hydrophobic surfaces to be exposed to the solvent or to other such protein molecules. And when the concentration of the synthesized protein increases, undesirable interactions between the hydrophobic surfaces of two or more protein molecules become more likely. Such interactions tend to defeat the goal of obtaining correctly folded proteins because protein molecules then agglomerate through these hydrophobic interactions.

With a ligand present on the surface of the solid matrix, however, each molecule that is in the process of folding into a functional protein molecule will then bind to a ligand, i.e., be adsorbed on the solid matrix, which is also termed an affinity matrix, and the correct conformation for the protein will be stabilized by interaction (bonding) of the protein with thin ligand. As the folding proceeds in the presence of the affinity matrix, each protein molecule will, therefore, be separated from every other protein molecule and achieve the proper folding so that the conformation of the protein molecule will be the same as that which is produced when a similar protein molecule is formed naturally within a cell.

These resultant properly folded protein molecules, of course, contrast with the inactive agglomerate of incompletely folded protein molecules that often results from the undesirable hydrophobic interactions when there are no ligands associated with a solid matrix within the reaction mixture.

After the reaction in the presence of the solid matrix, the protein can be eluted from the matrix by methods well known and widely used in the art of affinity chromatography. e.g., elution with the same soluble ligand in a buffer; elution with a different ligand, which can compete for protein binding with the immobilized ligand; elution with a buffer having a different pH from that used for the synthesis reaction; or elution under different ionic strength, different polarity of the elution buffer, etc. The pH value, the ionic strength, and the polarity of the elution buffer, when so utilized, are chosen to minimize the ligand-protein interactions. Another example of a well-known method for eluting the protein is dissociating the ligand. All these methods mentioned above for elution assure there be no protein denaturation.

It should be noted that the present technique for the In Vitro Biosynthesis of Proteins in Native Conformation is equally advantageous for biosynthesis in a batch mode or biosynthesis in a continuous-flow reactor.

However, as is well known in the art, a continuous-flow reactor will operate for a longer period of time than will a batch process, thereby producing a higher yield of proteins than will a batch process. In the present invention, low molecular weight substrates, such as amino acids and nucleotides, are delivered to the reaction mixture in an appropriate buffer through a membrane with very low porosity (e.g., a membrane with a molecular weight cut off between 500 and 10,000) in order not to let any of the proteins be eluted from the reaction mixture, as they appear to be in Spirin's reactor system. Improvement in the lifetime of the synthesis reaction, as compared to that associated with Spirin's reactor systems, is achieved because Spirin's system utilizes membranes with a molecular weight cut off of 30,000 to 300,000.

An example of the batch mode is:

EXAMPLE

Dihydrofolate reductase (DHFR) was synthesized in wheat germ extract—according to the protocol described in Schuler, M. A. and Zielinski, R. E. (1989) *Methods in Plant Molecular Biology,* pp. 97 through 105—using mRNA as a source of genetic information.

The mRNA was synthesized with the Ampliscribe SP6 Translation Kit (that is commercially available from Epicentre Technologies), according to the manufacturer's protocol, using 1 µg of linearized plasmid pSP65-DHFR.7 per 20 µl of transcription mixture. [The plasmid is described in Kudlicki, W.; Kramer, G.; and Hardesty, B. (1992) "High efficiency cell-free synthesis of proteins: Refinement of the coupled transcription/translation system," *Analytical Biochemistry* pp. 206, 389 through 393.]

The mRNA was used in translation without purification.

The quantity of mRNA which was utilized (1 µl in 40 µl of translation reaction) corresponded originally to 0.05 µg of DNA.

The translation mixture was supplemented with 4.8 µg of wheat germ tRNA and 64 units of rRNasin Rnase Inhibitor from Promega per 40 µl of reaction mixture.

The other components, viz., ATP, GTP, creatine phosphate, creatine phosphokinase, amino acids, $^{35}$S-methionine, buffer, and wheat germ extract, were added according to the Schuler and Zielinski protocol.

Three reactions were performed simultaneously: (1) a negative control without mRNA added, (2) a positive control with mRNA but without methotrexate-POROS [The terminology "methotrexate-POROS" is used herein to mean DHFR inhibitor methotrexate immobilized on the solid matrix POROS.], and (3) a reaction with mRNA and with methotrexate-POROS present in the ratio of 50 µl of the dry gel per 40 µl of the reaction mixture.

After completion of reaction (1) and reaction (2), methotrexate-POROS was added to the materials which were present; and the products of the reactions were analyzed as follows: Each reaction mixture was washed three times with 1 ml of translation buffer. After each wash, the mixture was centrifuged 1 minute at 2000 rpm; and 1 ml of the supernatant was removed before the next portion of the buffer was added. The final volume of the gel suspension was 100 µl, from which 10 µl was taken for electrophoresis.

DHFR was eluted from the methotrexate-POROS with 2.4 ml of 2 mM DHF in 50 mM Tris-HCl, pH 8, and 50 mM 2-mercaptoethanol. Eluate was concentrated—with Microcon-3 (3,000 molecular weight cut off) centrifugal concentrators which are commercially available from Amicon—to a volume of 90 µl, and 10 µl of the concentrate was analyzed by electrophoresis.

For reaction 2 and reaction 3, newly synthesized protein was detected as a single band in the gel phase and eluate; and the molecular weight of such newly synthesized protein corresponded to the molecular weight of DHFR. In the negative control [reaction 1], no bands were detected.

Moreover, the quantity of the DHFR eluted from the results of reaction 3 [the reaction when protein was synthesized in the presence of an immobilized ligand] was higher than the quantity of the protein which was bound to the methotrexate-POROS that had been introduced only after synthesis was completed [reaction 2].

We claim:

1. An improved batch method for the in vitro biosynthesis of proteins in native conformation, wherein the improvement comprises:

immobilizing on the surface of an affinity matrix at discrete locations a ligand for which the protein being synthesized has an affinity; and adding to the reaction mixture said affinity matrix having said immobilized ligand so that each molecule that is being synthesized into a functional protein molecule may bind an immobilized ligand and be kept separated from other protein molecules as the folding proceeds.

2. An improved continuous method for the in vitro biosynthesis of proteins in native conformation, wherein the improvement comprises:

immobilizing on the surface of an affinity matrix at discrete locations a ligand for which the protein being synthesized has an affinity; and adding to the reaction mixture said affinity matrix having said immobilized ligand so that each molecule that is being synthesized into a functional protein molecule may bind an immobilized ligand and be kept separated from other protein molecules as the folding proceeds.

* * * * *